United States Patent [19]

Nuber et al.

[11] Patent Number: 4,748,989

[45] Date of Patent: Jun. 7, 1988

[54] COPOLYMERS, USE THEREOF AS HAIR FIXATIVES AND HAIR FIXATIVES CONTAINING SAME

[75] Inventors: Adolf Nuber, Boehl-Iggelheim; Axel Sanner, Frankenthal; Friedrich Vogel, Wachenheim; Dietrich Mass, Mutterstadt, all of Fed. Rep. of Germany

[73] Assignee: BASF Aktiengesellschaft, Rheinland-Pfalz, Fed. Rep. of Germany

[21] Appl. No.: 79,944

[22] Filed: Jul. 31, 1987

[30] Foreign Application Priority Data

Aug. 18, 1986 [DE] Fed. Rep. of Germany ....... 3627969

[51] Int. Cl.$^4$ .............................................. A45D 7/00
[52] U.S. Cl. .......................................... 132/7; 424/71
[58] Field of Search ................ 132/7; 424/DIG. 1, 71

[56] References Cited

U.S. PATENT DOCUMENTS

| 3,715,428 | 2/1973 | Quasius et al. | 132/7 |
| 3,716,633 | 2/1973 | Viout | 132/7 |
| 3,790,664 | 2/1974 | Krochock et al. | 132/7 |
| 3,946,749 | 3/1976 | Papantoniou | 132/7 |

*Primary Examiner*—Gregory E. McNeill
*Attorney, Agent, or Firm*—Oblon, Fisher, Spivak, McClelland & Maier

[57] ABSTRACT

Copolymers of vinylpyrrolidone, acrylamides which are monoalkylated or dialkylated on the N atom and alkyl or hydroxyalkyl esters of (meth)acrylic acid, with or without (meth)acrylic acid, or (meth)acrylic acid are used as and in hair fixatives.

6 Claims, No Drawings

COPOLYMERS, USE THEREOF AS HAIR FIXATIVES AND HAIR FIXATIVES CONTAINING SAME

The present invention relates to a copolymer for use as a hair fixative and to hair fixatives containing same.

A very wide variety of polymers are used for hair cosmetics. Previously disclosed copolymer are frequently insufficiently compatible with the apolar alkane-based propellants used in hair sprays, which for ecological reasons are increasingly used as replacements for fluorohydrocarbons. In addition, in some cases the fixing action leaves something to be desired.

EP-B1-37,378 describes a resin which substantially meets the stated requirements but whose extraordinarily complicated and expensive preparation in the form of a precisely controlled solution polymerization is a disadvantage.

It is an object of the present invention to provide a very simple to prepare copolymer having particularly good hair-fixing properties and high compatibility, ie. solubility, with the halogen-free, apolar propellants propane and butane and a ready solubility in customary polar solvents, in particular alcohols.

We have found that this object is achieved with a copolymer which is obtained by free-radical polymerization and is defined in claims 1 to 3.

The present invention also provides a hair fixative containing the abovementioned copolymer, on which any carboxyl groups can be present in a neutralized or partially neutralized form, and the use thereof as a hair fixative.

N-mono- or N,N'-dialkylacrylamides are for example: N,N'-dimethylacrylamide, N,N'-diethylacrylamide, N,N'-dibutylacrylamide, N,N'-dipentylacrylamide, N-tert.-butyl acrylamide, N-sec.-butylacrylamide, N-n-butylacrylamide, N-n-octylacrylamide or N-tert.-octylacrylamide.

Of these, preference is given to N-tert.-butylacrylamide, N-n-octylacrylamide and N,N'-dimethylacrylamide and mixtures thereof.

Acrylic or methacrylic esters are for example methacrylate, methyl methacrylate, ethyl acrylate, ethyl methacrylate, tert.-butyl acrylate, tert.-butyl methacrylate, or hydroxypropyl acrylate in the form of its technical-grade mixture of 2- and 3-hydroxypropyl acrylate.

If acrylic acid or methacrylic acid are used as monomers, these carboxyl-containing monomers serve to improve the solubility in water, the carboxyl groups being partially, i.e. at least 50%, or completely, i.e. 100%, neutralized by an organic amine, preferably a mono-, di- or trialkanolamine having a total of 2 to 9 carbon atoms, such as 2-amino-2-methylpropanol, 2-amino-2-methyl-1,3-propanediol, triethanolamine or triisopropanolamine.

Where the monomer used is an acrylic ester which can reduce the solubility in water or aqueous solutions, the solubility-increasing vinylpyrrolidone content should in general be not less than 30%.

The copolymer according to the invention has the abovementioned defined K value and needs to be soluble in a lower alcohol of 1 to 4 carbon atoms, in particular ethanol and/or isopropanol. In the case of acrylic and/or methacrylic acid groups being present as copolymerized units, it should be soluble in a lower alcohol not only in the acid form but also in the neutralized or partially neutralized form defined above.

The copolymer according to the invention can be prepared by conventional solution, precipitation or suspension polymerization. Preference is given to a process where the monomers are slowly metered into a polymerizing mixture since in this way an advantageous course of the polymerization is ensured. The initiators used for the polymerization are the customary peroxides, such as benzoyl peroxide, tert-butyl perpivalate, tert.-butyl per-2-ethylhexanoate, di-tert.-butyl peroxide, tert.-butyl hydroperoxide and the like and also azo starters, such as azobisisobutyronitrile, in amounts of from 0.5 to 3% by weight, based on the weight of the monomers.

The K values are determined by the method of Fikentscher, Cellulosechemie 13(1932), 58–64, at 25° C. in a 1% strength by weight solution in ethanol, in the case of the carboxyl-containing copolymers in the acid form.

In addition, the copolymer according to the invention can be characterized in terms of its glass transition temperature, which should be at least about 60° C. The preferred range extends from 80° to 170° C.

The copolymer according to the invention is advantageously used as a hair fixative in the customary preparations and agents, any carboxyl groups being advantageously neutralized to from 50 to 100%, in a conventional manner together with any additional, customary additives, such as scents, plasticizers, dyes and the like. Preferred compositions are sprays and foams.

Particularly preferred hair fixing preparations are hair sprays based on ethanol and/or isopropanol as preferred solvents, if desired in combination with from 1.0 to 15.0% by weight of water or from 1.0 to 40.0% by weight of another solvent, such as methylene chloride or 1,1,1-trichloroethane.

Preferred combinations comprise from 1.0 to 5.0, preferably from 1.5 to 3, % by weight of a neutralized or partially neutralized copolymer, from 50 to 75% by weight of a solvent selected from the group consisting of a lower alkanol having 2 or 3 carbon atoms, methylene chloride or 1,1,1-trichloroethane and mixtures thereof and from 25 to 50% by weight of propane and/or butane as propellant. If desired, trichlorofluoromethane can be present as a propellant in small amounts, for example in an amount of up to 20% by weight, based on propellant.

The hair fixing preparations according to the invention generally contain, based on the total weight, from 0.5 to 5, preferably from 1.5 to 3, % by weight of copolymer.

Examples of preparation

EXAMPLE 1

A 1-liter flask equipped with a stirrer, reflux condenser and two dropping funnels is charged with 10% of a mixture of 180 parts of vinylpyrrolidone, 80 parts of N-tert.-butylacrylamide, 40 parts of ethyl acrylate and 300 parts of isopropanol and 10% of a mixture of 50 parts of isopropanol and 4.5 parts of tert.-butyl perpivalate, the contents are heated up to the boil, and the remaining 90% of the mixtures are added at a uniform rate with stirring in the course of 8 hours. The result is a clear yellowish viscous solution. On completion of the addition, the solution is left at the boil for a further two hours and cooled down.

The directions of Example 1 were followed to prepare the following polymers.

TABLE

| Example | 1 | 2 | 3 | 4 | 5 | 6 | 7 | 8 |
|---|---|---|---|---|---|---|---|---|
| | \multicolumn{8}{c}{Parts by weight} | | | | | | | |
| Vinylpyrrolidone | 180 | 90 | 120 | 120 | 150 | 100 | 75 | 90 | 85 |
| N,N'—dimethylacrylamide | — | — | — | 120 | — | 90 | 75 | 90 | 180 |
| N—n-butylacrylamide | — | — | — | — | 90 | — | 150 | — | — |
| N—tert.-butylacrylamide | 80 | 120 | — | — | — | 100 | — | — | — |
| N—n-octylacrylamide | — | — | 120 | — | — | — | — | — | — |
| Methyl acrylate | — | — | 30 | — | — | — | — | 120 | — |
| Methyl methacrylate | — | — | — | — | 60 | — | — | — | — |
| Ethyl acrylate | 40 | — | — | — | — | — | — | — | — |
| n-Butyl acrylate | — | 60 | — | — | — | — | — | — | — |
| tert.-Butyl acrylate | — | — | — | 60 | — | — | — | — | — |
| Acrylic acid | — | 30 | — | — | — | 10 | — | — | 35 |
| Methacrylic acid | — | — | 30 | — | — | — | — | — | — |

Examples of preparations

HAIR SPRAY FORMULATIONS

| | |
|---|---|
| 1. Copolymer of Example 1 | 2.0% by weight |
| Ethanol/isopropanol 50:50 | 68.0% by weight |
| Propane/butane 40:60 | 30.0% by weight |
| 2. Copolymer of Example 1 | 3.0% by weight |
| Ethanol | 57.0% by weight |
| Methylene chloride | 10.0% by weight |
| Propane/butane 40:60 | 30.0% by weight |
| 3. Copolymer of Example 1 | 2.0% by weight |
| Ethanol | 33.0% by weight |
| Methylene chloride | 35.0% by weight |
| Propane/butane 40:60 | 30.0% by weight |

We claim:

1. A copolymer for use as a hair fixative, obtained by free-radical polymerization of
   A. from 20 to 60% by weight of vinylpyrrolidone,
   B. from 20 to 60% by weight of an acrylamide which is monoalkylated or dialkylated at the N atom, with 1 to 8 carbon atoms in the alkyl, or mixtures thereof and
   C.
      from 5 to 60% by weight of an alkyl or hydroxylalkyl ester of acrylic or methacrylic acid having 1 to 4 carbon atoms in the alkyl or 2 to 4 carbon atoms in the hydroxyalkyl or mixtures thereof or
      from 3 to 12% by weight of acrylic acid or methacrylic acid or
      from 2 to 48% by weight of an alkyl or hydroxyalkyl ester of acrylic acid or methacrylic acid having 1 to 4 having atoms in the alkyl or 2 to 4 carbon atoms in' the hydroxyalkyl or mixtures thereof and
      from 3 to 12% by weight of acrylic acid or methacrylic acid,
   the % by weight being based on the total weight of the monomers,
   which is soluble in lower alcohols having 1 to 4 carbon atoms and has a K value of from 15 to 75.

2. A copolymer as claimed in claim 1, obtained by free-radical polymerization of
   A. from 30 to 50% by weight of vinylpyrrolidone,
   B. from 30 to 50% by weight of an acrylamide which is monoalkylated or dialkylated at the N atom, with 1 to 8 carbon atoms in the alkyl and
   C.
      from 20 to 40% by weight of an alkyl or hydroxyalkyl ester of acrylic or methacrylic acid having 1 to 4 carbon atoms in the alkyl or 2 to 4 carbon atoms in the hydroxyalkyl or mixtures thereof or
      from 5 to 10% by weight of acrylic acid or methacrylic acid or
      from 15 to 35% by weight of an alkyl or hydroxyalkyl ester of acrylic acid or methacrylic acid having 1 to 4 carbon atoms in the alkyl or 2 to 4 carbon atoms in the hydroxyalkyl or mixtures thereof and
      from 5 to 10% by weight of acrylic acid or methacrylic acid,
   which has a K value of from 20 to 50.

3. A copolymer as claimed in claim 1 or 2, whose free carboxyl groups are neutralized to from 50 to 100% by a mono-, di- or trialkanolamine having a total of 2 to 9 carbon atoms.

4. A hair fixative containing a copolymer as claimed in claim 1 or 2 or 3 as a film former.

5. A hair fixative as claimed in claim 4, containing the film former in an amount of from 0.5 to 5% by weight, based on the total weight.

6. A hair spray preparation as claimed in claim 4, containing, based on the total weight, from 1.0 to 5.0% by weight of a copolymer as claimed in claim 3, from 50% to 75% by weight of solvent and from 25 to 50% by weight of propellant.

* * * * *